United States Patent [19]

Eicken et al.

[11] Patent Number: 4,617,303

[45] Date of Patent: Oct. 14, 1986

[54] 7-AMINOZOLO [1,5-a] PYRIMIDINES AND FUNGICIDES CONTAINING THESE

[75] Inventors: Karl Eicken, Wachenheim; Hermann Graf, Mutterstadt; Walter Gramlich, Edingen-Neckarhausen; Hubert Sauter, Mannheim; Costin Rentzea, Heidelberg; Ernst-Heinrich Pommer, Limburgerhof; Eberhard Ammermann, Ludwigshafen, all of Fed. Rep. of Germany

[73] Assignee: BASF Aktiengesellschaft, Ludwigshafen, Fed. Rep. of Germany

[21] Appl. No.: 662,592

[22] Filed: Oct. 19, 1984

[30] Foreign Application Priority Data

Oct. 21, 1983 [DE] Fed. Rep. of Germany ....... 3338292

[51] Int. Cl.$^4$ .................... C07D 487/04; A01N 43/90
[52] U.S. Cl. .................................. 514/258; 544/263; 544/281
[58] Field of Search ............... 544/263, 281; 424/251; 514/258

[56] References Cited

U.S. PATENT DOCUMENTS

| 2,444,606 | 7/1948 | Heimbach et al. | 544/263 |
| 3,157,655 | 11/1964 | Takamizawa et al. | 544/281 |

FOREIGN PATENT DOCUMENTS

| 564048 | 7/1958 | Belgium | 544/263 |
| 1180329 | 1/1985 | Canada | 514/258 |
| 99794 | 8/1973 | Fed. Rep. of Germany | 544/263 |
| 2448542 | 5/1983 | France | 544/263 |
| 21854 | 10/1964 | Japan | 544/281 |
| 2673 | 2/1965 | Japan | 544/281 |
| 24377 | 10/1965 | Japan | 544/281 |
| 1148629 | 4/1969 | United Kingdom | 544/263 |

OTHER PUBLICATIONS

Eicken, K., et al., Chemical Abstract, 98: 215609q, (1983) of German Pat. No. 3,130,633.
Takamizawa, A., Chemical Abstract, 68: 95842s (1968).
Levin, A., et al., Chemical Abstract, 60: 523d (1964).
J. Pharm. Soc. Japan, vol. 84, pp. 1113 to 1118 (1964).

Primary Examiner—George F. Lesmes
Assistant Examiner—S. Gibson
Attorney, Agent, or Firm—Keil & Weinkauf

[57] ABSTRACT

7-Aminoazolo[1,5-a]pyrimidines of the formula

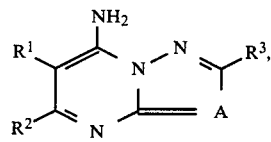

where
$R^1$ is alkyl or aralkyl,
$R^2$ and $R^3$ are each hydrogen or alkyl, and
A is nitrogen or $CR^4$, where
$R^4$ is hydrogen, alkyl or halogen, and fungicides containing these compounds.

7 Claims, No Drawings

7-AMINOAZOLO [1,5-a] PYRIMIDINES AND FUNGICIDES CONTAINING THESE

The present invention relates to novel 7-aminoazolo-[1,5-a]pyrimidines, processes for their preparation and fungicides containing these compounds.

It has been disclosed that 7-aminoazolo[1,5-a]-pyrimidines possess pharmacological properties (French Pat. No. 2,448,542, East German Pat. Nos. 99,794 and 55,956, and J. pharm. Soc. Japan 84 (1964), 1113–1118).

We have found that novel 7-aminoazolo[1,5-a]pyrimidines of the formula

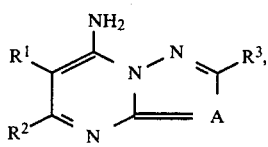

where $R^1$ is alkyl which is unsubstituted or substituted by alkoxy or halogen or is aralkyl which is unsubstituted or substituted in the aryl moiety by alkyl, alkoxy or halogen, $R^2$ and $R^3$ are each hydrogen or alkyl, and A is nitrogen or $CR^4$, where $R^4$ is hydrogen, alkyl or halogen, have a good fungicidal action, in particular against phycomycetes.

$R^1$ is, for example, $C_4$–$C_{18}$-alkyl, eg. $C_4$–$C_8$-alkyl, which is unsubstituted or substituted by fluorine, chlorine, bromine, or $C_1$–$C_{18}$-alkoxy, or is aralkyl where alkyl is of 1 to 12 carbon atoms, eg. benzyl, p-butylbenzyl or 3-phenylpropyl, which can be substituted in the aryl moiety by $C_1$–$C_4$-alkyl, $C_1$–$C_4$-alkoxy, fluorine, chlorine or bromine.

$R^2$, $R^3$ and $R^4$ are each, for example, hydrogen or $C_1$–$C_4$-alkyl, eg. methyl, and $R^4$ may furthermore be, for example, chlorine or bromine.

Alkyl, or the alkyl moiety of an alkoxy group is, depending on the stated number of carbon atoms, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl or octadecyl or an isomer of one of these.

We have furthermore found that 7-aminoazolo[1,5-a]-pyrimidines of the formula I are obtained if a substituted , β-keto ester of the formula II

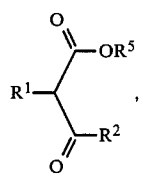

where $R^1$ and $R^2$ have the above meanings and $R^5$ is a lower alkyl radical, is reacted with an aminoazole of the formula III

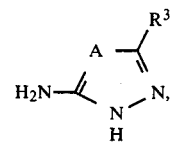

where A, $R^3$ and $R^4$ have the above meanings, to give a condensate of the formula V

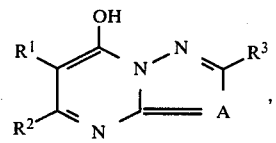

where $R^1$, $R^2$, $R^3$ and A have the above meanings, this condensate is subjected to a halogenation reaction in which the hydroxyl group is replaced by halogen, and the product is reacted with ammonia.

The β-keto esters can be prepared as described in Organic Synthesis Coll. Vol. 1, page 248.

The reaction of the substituted β-keto esters of the formula II with the aminoazoles of the formula III can be carried out in the presence or absence of a solvent. It is advantageous to use a solvent which is substantially inert towards the starting materials and in which the latter are partially or completely soluble. Particularly suitable solvents are alcohols, such as ethanol, propanols, butanols, glycols, glycol monoethers or diethylene glycols or their monoethers, amides, such as dimethyl formamide, diethyl formamide, dibutyl formamide or N,N-dimethylacetamide, lower alkanoic acids, such as formic acid, acetic acid or propionic acid, and mixtures of these solvents with water. The reaction temperatures are from 50° to 300° C., preferably from 50° to 150° C., when the reaction is carried out in solution.

The condensates of the formula V which are obtained in this manner are precipitated from the reaction solutions in general in pure form, and are washed with the same solvent or with water, dried, and then halogenated with halogenating agents, in particular chlorinating agents, eg. phosphorus chlorides, preferably phosphorus oxytrichloride, at from 50° to 150° C., preferably in excess phosphorus oxytrichloride under reflux. After the excess phosphorus oxytrichloride has been evaporated, the residue is treated with ice water, with or without the addition of a water-immiscible solvent. The chlorination product which is isolated from the dry organic phase, if necessary after evaporation of the inert solvent, is generally very pure; it is then reacted with ammonia in an inert solvent at from 100° to 200° C. to give the novel 7-aminoazolo-[1,5-a]pyrimidine. The reaction is preferably carried out under from 1 to 100 bar, using a 1–10 molar excess of ammonia.

The novel 7-aminoazolo[1,5-a]pyrimidines are isolated as crystalline compounds which are generally very pure, by evaporating the solvent if necessary and then making a paste with water.

We have furthermore found that 7-aminoazolo[1,5-a]-pyrimidines of the formula I are obtained if a substituted benzyl cyanide of the formula

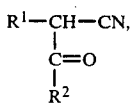

where $R^1$ and $R^2$ have the above meanings, is reacted with an aminoazole of the formula III

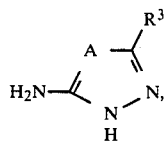

where A, $R^3$ and $R^4$ have the above meanings.

The reaction can be carried out in the presence or absence of a solvent. It is advantageous to use a solvent which is substantially inert toward the starting materials and in which the latter are partially or completely soluble. Particularly suitable solvents are alcohols, such as ethanol, propanols, butanols, glycols, glycol monoethers or diethylene glycols or their monoethers, amides, such as dimethylformamide, diethylformamide, dibutylformamide or N,N-dimethylacetamide, lower alkanoic acids, such as formic acid, acetic acid or propionic acid, and mixtures of these solvents with water. The reaction temperatures are from 50° to 300° C., preferably from 50° to 150° C., when the reaction is carried out in solution.

The novel 7-aminoazolo[1,5-a]pyrimidines are isolated as crystalline compounds, which are generally very pure, if necessary after evaporation of the solvent or dilution with water. Where lower alkanoic acids are used as solvents, it is advantageous to neutralize the remainder of the alkanoic acid by adding an aqueous alkali, if necessary after partial evaporation of the alkanoic acid; the novel 7-aminoazolo[1,5-a]pyrimidines generally crystallize out in very pure form.

Some of the substituted alkyl cyanides of the formula

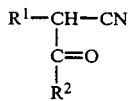

which are required for the preparation of the 7-aminoazolo[1,5-a]pyrimidines are known; those which are unknown can be prepared by conventional methods, from an alkyl cyanide and a carboxylate with a strong base, eg. an alkali metal hydride, an alkali metal amide or a metalalkyl (J. Amer. Chem. Soc. 73, (1951), 3766).

General methods of preparation for the substituted alkyl cyanides of the formula VI 1.5 moles of sodium hydride are introduced into 1 liter of toluene, and 1.0 mole of an alkyl cyanide followed by 2.0 moles of a carboxylate are then added dropwise to the stirred mixture, the temperature increasing to 40°–50° C. Stirring is continued for 2 hours at from 75° to 80° C., after which the mixture is cooled and 2 liters of water are added. The aqueous phase is washed twice with 0.2 liters of toluene and acidified with semiconcentrated (about 50% strength by weight) sulfuric acid to pH 2, and the substituted alkyl cyanide of the formula VI is then isolated from the aqueous phase.

EXAMPLES

1. Preparation of 7-amino-2,5-dimethyl-6-n-octylpyrazolo[1,5-a]pyrimidine (Compound 2)

(a) 7-hydroxy-2,5-dimethyl-6-n-octylpyrazolo[1,5-a]-pyrimidine 200 g of methyl 2-n-octylacetoacetate and 94 g of 3(5)-amino-5(3)-methylpyrazole in 400 ml of n-butanol are refluxed for 5 hours. The mixture is cooled, and the product is filtered off under suction, washed with cold methanol and dried under reduced pressure at 60° C. to give 191 g of 7-hydroxy-2,5-dimethyl-6-n-octylpyrazolo[1,5-a]pyrimidine of melting point 199° C.

(b) 7-chloro-2,5-dimethyl-6-n-octylpyrazolo[1,5-a]-pyrimidine 190 g of the condensate obtained from (a), in 550 ml of phosphorus oxytrichloride, are refluxed for 1.5 hours, after which the excess phosphorus oxytrichloride is evaporated under reduced pressure and the residue is stirred with 500 ml of $CH_2Cl_2$ and 500 ml of ice water. The organic phase is separated off, washed with three times 100 ml of ice water, dried over sodium sulfate and filtered, the solvent is evaporated under reduced pressure, and 179 g of 7-chloro-2,5-dimethyl-6-n-octylpyrazolo-[1,5-a]pyrimidine are isolated as a viscous mass.

(c) 7-amino-2,5-dimethyl-6-n-octylpyrazolo[1,5-a]-pyrimidine 179 g of the chloride obtained in b) and 1300 ml of ethanol are introduced into a 2.5 liter autoclave, 85 g of ammonia are forced in, and the mixture is stirred at 150° C. and under 30 bar for 8 hours. The reacted mixture is concentrated under reduced pressure, the residue is made into a paste with 1000 ml of water, and the product is filtered off under suction and dried under reduced pressure at 70° C. to give 133 g of 7-amino-2,5-dimethyl-6-n-octylpyrazolo-[1,5-a]pyrimidine of melting point 169° C. (Compound 2).

2. Preparation of 7-amino-6-n-butyl-5-methyl-1,2,4-triazolo[1,5-a]pyrimidine (Compound 34)

(a) 2-acetyl-n-capronitrile 11.7 g (300 millimoles) of powdered sodium amide are introduced into 500 ml of liquid ammonia at −60° C., and a mixture of 29.1 g (300 millimoles) of n-capronitrile and 26.4 g (300 millimoles) of ethyl acetate is then added slowly. Stirring is continued for 2 hours at −60° C., 200 ml of diethyl ether are added, and the mixture is left overnight to warm up to room temperature, gaseous ammonia escaping. First water and then 50% strength sulfuric acid are added, while cooling with ice, until the pH reaches 5. The ether phase is separated off, the aqueous phase is extracted twice with ether, the combined organic phases are dried and evaporated down, and the remaining oil (40 g; 96% crude yield) is distilled under reduced pressure. The fraction passing over at 52° C./0.4 mbar has a purity higher than 98% according to gas chromatography.

(b) 9.0 g (65 millimoles) of the nitrile from Example 2a and 5.5 g (65 millimoles) of 3-amino-1,2,4-triazole in 200 ml of propionic acid are refluxed for 12 hours, after which the solution is allowed to cool and is then evaporated down to one third of its initial volume. After some time, a precipitate is formed; this is filtered off, washed with a little 2N NaOH and water, and recrystallized from ethanol. Yield: 8.6 g (65%), m.p.: 246° C. (Compound 34).

3. Preparation of 7-amino-6-n-butyl-2-methyl-5-n-propylpyrazolo[1,5-a]pyrimidine (Compound 24)

(a) 2-n-butyryl-n-capronitrile 29.1 g (300 millimoles) of n-capronitrile are reacted with 34.8 g (300 millimoles) of ethyl n-butyrate, as described in Example 2a. Crude yield: 98%, yield of pure compound: 50%, bp.: 94° -95° C./0.2 mbar.

(b) 10.1 g (60.5 millimoles) of the nitrile obtained in 3a and 5.80 g (300 millimoles) of 3(5)-amino-5(3)-methyl-pyrazole are reacted as described in Example 2b. Yield: 5.0 g (34%), mp. (from ethanol): 167° C. (Compound 24).

4. Preparation of 7-amino-5-methyl-6-[3-(n-nonyloxy)propyl]-1,2,4-triazolo[1,5-a]pyrimidine (Compound 44)

(a) 2-acetyl-5-(n-nonyloxy)-valeronitrile 35.0 g (156 millimoles) of 5-(n-nonyloxy)-valeronitrile in 500 ml of absolute tetrahydrofuran are initially taken, in the absence of water and under an inert gas atmosphere, and the mixture is cooled to −60° C. 162 millimoles of n-butyl-lithium in n-hexane are slowly added to the stirred mixture, which is then left for 4 hours at −60° C. A solution of 13.1 g (155 millimoles) of dry ethyl acetate in tetrahydrofuran is then added dropwise, stirring is continued for 3 hours at −60° C., and the mixture is allowed to warm up slowly to room temperature. First water and then 2N hydrochloric acid are added while cooling with ice, until the pH of the solution reaches 4. The organic phase which separates out is isolated, washed with water, dried and evaporated down. The oil which remains (41 g; 99%) is more than 90% pure according to gas chromatography, and can be reacted without further purification.

(b) 20.0 g (75 millimoles) of the nitrile from Example 4a are reacted with 6.30 g (75 millimoles) of 3-amino-1,2,4-triazole in 300 ml of boiling propionic acid for 16 hours. The mixture is cooled, the solution is separated off from the precipitate, the filtrate is evaporated down, the residue is taken up in water, the solution is extracted several times with dichloromethane, the combined organic phases are dried and evaporated down, and the oily residue is triturated with diethyl ether to give 9.0 g (36%) of a crystalline compound of melting point 167° C. (Compound 44).

5. Preparation of 7-amino-5-methyl-6-[3-(neo pentyloxy)-propyl] 1,2,4-triazolo[1,5-a]pyrimidine (Compound 38)

(a) 7-hydroxy-5-methyl-6-[3-(neopentyloxy)-propyl]-1,2,4-triazolo[1,5-a]pyrimidine 22.0 g (90 millimoles) of methyl 2-[3-(neopentyloxy)-propyl]-acetoacetate and 7.14 g (84.9 millimoles) of 3-amino -1,2,4-triazole in 300 ml of boiling propionic acid are allowed to react for 21 hours. The mixture is cooled and then evaporated down, the residue is stirred into ice water, the solution is neutralized with 2N NaOH, and the product is filtered off under suction to give 13.5 g (57%) of colorless crystals of melting point 155°–159° C., which are reacted without further purification.

(b) 7-chloro-5-methyl-6-[3-(neopentyloxy)-propyl]-1,2,4-triazolo[1,5-a]pyrimidine 11.5 g (41.4 millimoles) of the product from 5a, in 330 ml of phosphorus oxytrichloride, are refluxed for 8 hours, after which volatile components are distilled off, the oily residue which remains is taken up in dichloromethane, and the solution is washed with saturated sodium bicarbonate solution, dried and evaporated down to give 10 g (82%) of a yellowish oil which is pure according to thin layer chromatography.

(c) 10.0 g (33.7 millimoles) of the product from 5b are dissolved in 100 ml of dioxane, and then reacted with 6.3 g (370 millimoles) of ammonia in an autoclave at 130° C. for 60 hours. After the mixture has been cooled and the pressure let down, the resulting precipitate is filtered off under suction and taken up in dichloromethane, and the solution is washed three times with water, dried and evaporated down to give 5.5 g (58%) of a colorless powder (compound 38) of melting point 202° C. A further 2.5 g of product can be obtained by evaporating down the filtrate from the dioxane solution.

For example, the following 7-aminoazolo[1,5-a]pyrimidines can be prepared by the methods described above:

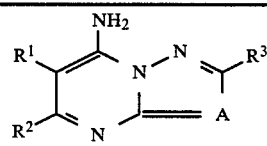

| No. | R¹ | R² | R³ | R⁴ | A | M.p. (°C.) |
|---|---|---|---|---|---|---|
| 1 | n-C$_4$H$_9$ | CH$_3$ | CH$_3$ | H | CR$^4$ | 186 |
| 2 | n-C$_8$H$_{17}$ | CH$_3$ | CH$_3$ | H | CR$^4$ | 169 |
| 3 | n-C$_4$H$_9$—CH(C$_2$H$_5$)—CH$_2$ | CH$_3$ | CH$_3$ | H | CR$^4$ | 159 |
| 4 | n-C$_8$H$_{17}$ | CH$_3$ | H | — | N | 217 |
| 5 | n-C$_4$H$_9$—CH(C$_2$H$_5$)—CH$_2$ | CH$_3$ | H | — | N | 228 |
| 6 | C$_6$H$_5$—CH$_2$ | CH$_3$ | CH$_3$ | H | CR$^4$ | 235 |
| 7 | 4-t.C$_4$H$_9$—C$_6$H$_4$—CH$_2$ | CH$_3$ | CH$_3$ | H | CR$^4$ | 214 |
| 8 | 4-t.C$_4$H$_9$—C$_6$H$_4$—CH$_2$ | CH$_3$ | H | — | N | >280 |
| 9 | C$_6$H$_5$—(CH$_2$)$_3$ | CH$_3$ | H | — | N | 244 |
| 10 | n-C$_5$H$_{11}$ | CH$_3$ | H | — | N | 251 |

-continued

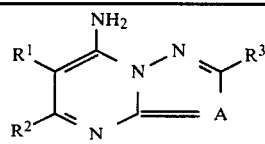

| No. | R$^1$ | R$^2$ | R$^3$ | R$^4$ | A | M.p. (°C.) |
|---|---|---|---|---|---|---|
| 11 | n-C$_6$H$_{13}$ | CH$_3$ | H | — | N | 237 |
| 12 | n-C$_7$H$_{15}$ | CH$_3$ | H | — | N | 209 |
| 13 | n-C$_5$H$_{11}$ | CH$_3$ | CH$_3$ | — | N | 193 |
| 14 | n-C$_6$H$_{13}$ | CH$_3$ | CH$_3$ | — | N | 200 |
| 15 | n-C$_8$H$_{17}$ | CH$_3$ | CH$_3$ | — | N | 198 |
| 16 | n-C$_4$H$_9$ | n-C$_4$H$_9$ | H | — | N | 187 |
| 17 | n-C$_4$H$_9$ | n-C$_4$H$_9$ | CH$_3$ | H | CR$^4$ | 145 |
| 18 | N—C$_3$H$_7$—CH(CH$_3$)—CH$_2$ | CH$_3$ | H | — | N | 209 |
| 19 | N—C$_3$H$_7$—CH(CH$_3$)—CH$_2$ | CH$_3$ | CH$_3$ | H | CR$^4$ | 176 |
| 20 | (H$_5$C$_2$)$_2$—CH—CH$_2$ | CH$_3$ | CH$_3$ | H | CR$^4$ | 178 |
| 21 | n-C$_{10}$H$_{21}$ | n-C$_3$H$_7$ | H | — | N | 152 |
| 22 | n-C$_{10}$H$_{21}$ | n-C$_3$H$_7$ | CH$_3$ | H | CR$^4$ | 114 |
| 23 | N—C$_{10}$H$_{21}$ | n-C$_4$H$_9$ | H | — | N | 151 |
| 24 | n-C$_5$H$_9$ | n-C$_3$H$_7$ | CH$_3$ | H | CR$^4$ | 167 |
| 25 | n-C$_4$H$_9$ | n-C$_3$H$_7$ | H | — | N | 186 |
| 26 | n-C$_{12}$H$_{25}$ | CH$_3$ | CH$_3$ | — | CR$^4$ | 127 |
| 27 | n-C$_{12}$H$_{25}$ | CH$_3$ | H | — | N | 209 |
| 28 | n-C$_{10}$H$_{21}$ | CH$_3$ | H | — | N | 207 |
| 29 | n-C$_9$H$_{19}$ | CH$_3$ | H | — | N | 215 |
| 30 | n-C$_6$H$_{13}$ | CH$_3$ | CH$_3$ | H | CR$^4$ | 177 |
| 31 | n-C$_9$H$_{19}$ | CH$_3$ | CH$_3$ | — | N | 159 |
| 32 | n-C$_{10}$H$_{21}$ | CH$_3$ | CH$_3$ | H | CR$^4$ | 146 |
| 33 | 4-t-C$_4$H$_9$—C$_6$H$_4$—CH$_2$—CH(CH$_3$) | CH$_3$ | H | — | N | 256 |
| 34 | n-C$_4$H$_9$ | CH$_3$ | H | — | N | 246 |
| 35 | (n-C$_3$H$_7$)(C$_2$H$_5$)CHCH$_2$—O—(CH$_2$)$_3$ | CH$_3$ | CH$_3$ | H | CR$^4$ | 108 |
| 36 | (n-C$_3$H$_7$)(C$_2$H$_5$)CHCH$_2$—O—(CH$_2$)$_3$ | CH$_3$ | H | — | N | 149 |
| 37 | t-C$_4$H$_9$CH$_2$—O—(CH$_2$)$_3$ | CH$_3$ | CH$_3$ | H | CR$^4$ | 134 |
| 38 | t-C$_4$H$_9$—CH$_2$—O—(CH$_2$)$_3$ | CH$_3$ | H | — | N | 202 |
| 39 | t-C$_4$H$_9$—O—(CH$_2$)$_4$ | CH$_3$ | CH$_3$ | H | CR$^4$ | 61 (decomposes) |
| 40 | (t-C$_4$H$_9$—CH$_2$)(CH$_3$)CH(CH$_2$)$_2$—O—(CH$_2$)$_5$ | CH$_3$ | H | — | N | 161 |
| 41 | (i-C$_4$H$_9$)(C$_2$H$_5$)CH—O—(CH$_2$)$_3$ | CH$_3$ | H | — | N | 156 |
| 42 | n-C$_8$H$_{17}$—O—(CH$_2$)$_3$ | n-C$_3$H$_7$ | H | — | N | 97 |
| 43 | i-C$_3$H$_7$—(CH$_2$)$_3$—CH(CH$_3$)—(CH$_2$)$_2$—O—(CH$_2$)$_3$ | CH$_3$ | H | — | N | 156 |
| 44 | n-C$_9$H$_{19}$—O—(CH$_2$)$_3$ | CH$_3$ | H | — | N | 167 |
| 45 | n-C$_4$H$_9$—O—(CH$_2$)$_3$ | CH$_3$ | H | — | N | 180 |
| 46 | n-C$_6$H$_{13}$—O—(CH$_2$)$_3$ | CH$_3$ | H | — | N | 176 |
| 47 | n-C$_9$H$_{19}$—O—(CH$_2$)$_3$ | CH$_3$ | CH$_3$ | H | CR$^4$ | 94 |
| 48 | n-C$_6$H$_{13}$—O—(CH$_2$)$_3$ | n-C$_3$H$_7$ | H | — | N | 109 |
| 49 | (n-C$_4$H$_9$)(C$_2$H$_5$)CH—CH$_2$—O—(CH$_2$)$_5$ | CH$_3$ | H | — | N | resin |
| 50 | t-C$_4$H$_9$—CH$_2$—CH(CH$_3$)—(CH$_2$)$_2$—O—(CH$_2$)$_3$ | CH$_3$ | H | — | N | 154 |
| 51 | n-C$_4$H$_9$—O—(CH$_2$)$_3$ | CH$_3$ | CH$_3$ | H | CR$^4$ | 145 |
| 52 | t-C$_4$H$_9$—CH$_2$—CH(CH$_3$)—(CH$_2$)$_2$—O—(CH$_2$)$_3$ | CH$_3$ | CH$_3$ | H | CR$^4$ | 122 |

The novel active ingredients have a strong fungitoxic action on phytopathogenic fungi, especially from the Phycomycetes class. The novel compounds are therefore suitable for instance for combating *Phytophthora infestans* in tomatoes and potatoes, *Phytophthora parasitica* in strawberries, *Phytophthora cactorum* in apples, *Pseudoperonospora cubensis* in cucumbers, *Pseudoperonospora humuli* in hops, *Peronospora destructor* in onions, *Peronospora sparsa* in roses, *Peronospora tabacina* in tobacco, *Plasmopara viticola* in graphes, *Plasmopara halstedii* in sunflowers, *Sclerospora macrospora* in Indian corn, *Bremia lactucae* in lettuce, *Mucor mucedo* in fruit, *Rhizopus nigricans* in beets, *Erysiphe graminis* in cereals, *Uncinula necator* in grapes, *Podosphaera leucotricha* in apples, *Sphaerotheca fuliginea* in roses, and *Erysiphe cichoriacearum* in cucumbers.

The active ingredients are excellently tolerated by plants. Some of the active ingredients also have curative properties, i.e., the agents may be applied after infection of the plants by the pathogen and success is still ensured.

The fungicidal agents contain from 0.1 to 95, and preferably from 0.5 to 90, wt % of active ingredient. The application rates depend on the type of effect desired, and range from 0.1 to 5 kg of active ingredient per hectare.

The novel active ingredients may also be mixed and applied with other active ingredients, e.g., herbicides, insecticides, growth regulators, other fungicides and fertilizers. When mixed with other fungicides, the spectrum of fungicidal action is in many cases increased; with a number of these fungicidal compositions, synergistic effects also occur, i.e., the fungicidal action of the combination product is greater than the effect of the individual components added together. Examples of fungicides which can be combined with the novel compounds are as follows:

sulfur
dithiocarbamates and derivatives thereof, such as
ferric dimethyldithiocarbamate
zinc dimethyldithiocarbamate
zinc ethylenebisthiocarbamate
tetramethylthiuram disulfide
manganese-zinc ethylenediamine-bisdithiocarbamate
ammonia complex of zinc-(N,N'-ethylene)-bisdithiocarbamate
and
N,N'-polyethylene-bis-(thiocarbamoyl)-disulfide
ammonia complex of zinc-(N,N'-propylene-bisdithiocarbamate)
and
N,N'-polypropylene-bis-(thiocarbamoyl)-disulfide
nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
diisopropyl 5-nitroisophthalate
heterocyclic structures, such as
2-heptadecyl-2-imidazoline acetate
2,4-dichloro-6-(o-chloroanilino)-s-triazine
0,0-diethylphthalimidophosphorothionate
5-amino-1-[bis-(dimethylamino)-phosphynyl]-3-phenyl-1,2,4-triazole
2,3-dicyano-1,4-dithiaanthraquinone
2-thio-1,3-dithio-(4,5-b)-quinoxaline
methyl 1-(butylcarbamoyl)-2-benzimidazole carbamate
2-methoxycarbonylaminobenzimidazole
2-[furyl-(2)]-benzimidazole
2-[thiazolyl-(4)]-benzimidazole
N-(1,1,2,2-tetrachloroethylthio)-tetrahydrophthalimide
N-trichloromethylthiotetrahydrophthalimide
N-trichloromethylphthalimide
N-dichlorofluoromethylthio-N',N'-dimethyl-N-phenyl-sulfuric acid diamide
5-ethoxy-3-trichloromethyl-1,2,3-thiadiazole
2-thiocyanomethylthiobenzthiazole
1,4-dichloro-2,5-dimethoxybenzene
4-(2-chlorophenylhydrazono)-3-methyl-5-isoxazolone
pyridine-2-thio-1-oxide
8-hydroxyquinoline and its copper salt
2,3-dihydro-5-carboxanilido-6-methyl-1,4-oxathiin-4,4-dioxide
2,3-dihydro-5-carboxanilido-6-methyl-1,4-oxathiin
2-methyl-5,6-dihydro-4-H-pyran-3-carboxanilide
2-methyl-furan-3-carboxanilide
2,5-dimethyl-furan-3-carboxanilide
2,4,5-trimethyl-furan-3-carboxanilide
2,5-dimethyl-furan-3-carboxylic acid cyclohexylamide
N-cyclohexyl-N-methoxy-2,5-dimethyl-furan-3-carboxamide
2-methyl-benzoic acid anilide
2-iodobenzoic anilide
N-formyl-N-morpholine-2,2,2-trichloroethylacetal
piperazine-1,4-diylbis-(1-(2,2,2-trichloroethyl)-formamide
1-(3,4-dichloroanilino)-1-formylamino-2,2,2-trichlorethane
2,6-dimethyl-N-tridecyl-morpholine and its salts
2,6-dimethyl-N-cyclododecyl-morpholine and its salts
N-[3-(p-tert.-butylphenyl)-2-methylpropyl]-cis-2,6-dimethylmorpholine
N-[3-(p-tert.-butylphenyl)-2-methylpropyl]-piperidine
1-[2-(2,4-dichlorophenyl)-4-ethyl-1,3-dioxolan-2-yl-ethyl]-1-H-1,2,4-triazole -1,2,4-triazole
-[2-(2,4-dichlorophenyl)-4-n-propyl-1,3-dioxolan-2-yl-ethyl]-1-H-1,2,4-triazole
N-(n-propyl)-N-(2,4,6-trichlorophenoxyethyl)-N'-imidazol-ylurea
1-(4-chlorophenoxy)-3,3-dimethyl-1-(1H-1,2,4-triazol-1-yl)-2-butanone
1-(4-chlorophenoxy)-3,3-dimethyl-1-(IH-1,2,4-triazol-1-yl)-2-butanol
alpha-(2-chlorophenyl)-alpha-(4-chlorophenyl)-5-pyrimidinemethanol
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl)-2-thioureido)-benzene
2-cyano-N-(ethylaminocarbonyl)-2-(methoximino)-acetamide
and various fungicides, such as
dodecylguanidine acetate
3-[2-(3,5-dimethyl-2-oxycyclohexyl)-2-hydroxyethyl]-glutarimide
hexachlorobenzene
D,L-methyl-N-(2,6-dimethylphenyl)-N-(2-furoyl)-alanate
methyl D,L-N-(2,6-dimethylphenyl)-N-(2-methoxyacetyl)-alanate
N-(2,6-dimethylphenyl)-N-chloroacetyl-D,L-2-aminobutyrolactone
methyl DL-N-(2,6-dimethylphenyl)-N-(phenylacetyl)-alanate 5-methyl-5-vinyl-3-(3,5-dichlorophenyl)-2,4-dioxo-1,3-oxazolidine
3-(3,5-dichlorophenyl)-5-methyl-5-methoxymethyl-1,3-oxazolidine2,4-dione
3-(3,5-dichlorophenyl)-1-isopropyl-carbamoylhydantoin
N-(3,5-dichlorophenyl)-1,2-dimethyl-cyclopropane-1,2-dicarboximide.

The novel active ingredients are applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the novel active ingredients as possible.

For the preparation of solutions, emulsions, pastes and oil dispersions to be used direct, mineral oil fractions of medium to high boiling point, such as kerosene or diesel oil, further coal-tar oils, and oils of vegetable or animal origin, aliphatic, cyclic and aromatic hydrocarbons carbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, and N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

Examples of such formulations follow.

I. 90 parts by weight of the compound of Example 1 is mixed with 10 parts by weight of N-methyl-alpha-pyrrolidone. A mixture is obtained which is suitable for application in the form of very fine drops.

II. 20 parts by weight of the compound of Example 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of the compound of Example 1 is dissolved in a mixture consisting of 30 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of the compound of Example 2 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 20 parts by weight of the compound of Example 1 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in water, a spray liquor is obtained.

VI. 5 parts by weight of the compound of Example 2 is intimately mixed with 95 parts by weight of particulate kaolin. A dust is obtained containing 5% by weight of the active ingredient.

VII. 30 parts by weight of the compound of Example 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of the compound of Example 2 is intimately mixed with 30 parts of the sodium salt of a phenolsulfonic acid-urea-formaldehyde condensate, 2 parts of silica gel and 48 parts of water to give a stable aqueous dispersion.

IX. 20 parts of the compound of Example 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The following experiments demonstrate the biological action of the novel compounds.

EXAMPLE 1

Action on *Plasmopara viticola*

Leaves of potted vines of the Mü ller-Thurgau variety were sprayed with aqueous suspensions containing (dry basis) 80% of active ingredient and 20% of emulsifier. To assess the duration of action, the plants were set up, after the sprayed-on layer had dried, for 10 days in the greenhouse. Then the leaves were infected with a zoospore suspension of Plasmopara viticola. The plants were first placed for 16 hours in a water vapor-saturated chamber at 24° C. and then in a greenhouse for 8 days at from 20° to 30° C. To accelerate and intensify the sporangiophore discharge, the plants were then again placed in the moist chamber for 16 hours. The extent of fungus attack was then assessed on the undersides of the leaves.

The results of the experiment show that for instance compounds nos. 1, 2, 3, 4, 5, 9, 10, 11, 12, 13, 14, 15, 16, 17, 18, 19, 20, 21, 22, 25, 26, 28, 29, 30, 31 and 32, applied as 0.05 and 0.025% spray liquors, had a better fungicidal action (e.g., 97%) than the prior art active ingredients 7-amino-6-phenyl-(1,2,4-triazolo)-[1,5-a]-pyrimidine (A) and 7-amino-2-methyl-6-phenyl-pyrazolo-[1,5-a]-pyrimidine (B) (e.g., 30%).

EXAMPLE 2

Action of *Phytophthora infestans* in tomatoes

Leaves of potted tomatoes of the "Groe Fleischtomate" variety were sprayed with aqueous liquors containing (dry basis) 80% of active ingredient and 20% of emulsifier. After the sprayed-on layer had dried, the leaves were infected with a zoospore suspension of Phytophthora infestans. The plants were then placed for 5 days in a steam-saturated chamber kept at 16° to 18° C. After this period, the disease had spread on the untreated control plants to such an extent that the fungicidal action of the compounds was able to be assessed.

The results of this experiment show that for example compounds nos. 4, 5, 10, 11, 13, 14, 15, 16, 18, 19, 20, 21, 25, 29, 33, 36, 40, 41, 48 and 49, applied as 0.025% spray liquors, had a better fungicidal action (e.g., 90%) than the prior art active ingredients A and N-trichloromethylthio-tetrahydrophthalimide (e.g., 60%).

We claim:

1.

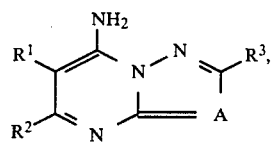

I where
- $R^1$ is a $C_6$–$C_{18}$-alkyl which is unsubstituted or a $C_3$–$C_{18}$ alkyl which is mono substituted by a $C_1$–$C_{18}$-alkoxy or halogen and
- $R^2$ and $R^3$ are each hydrogen or a $C_1$–$C_4$-alkyl, and A is nitrogen or $CR^4$, where
- $R^4$ is hydrogen, a $C_1$–$C_4$ alkyl or halogen.

2. A process for combatting fungi, wherein the fungi or the materials, plants, soils or seeds to be protected against fungus attack are treated with a fungicidally effective amount of an aminoazolopyrimidine of the formula

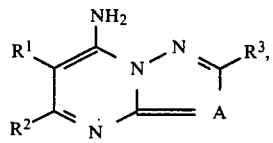

I where
- $R^1$ is a $C_4$–$C_{18}$-alkyl which is unsubstituted or mono substituted by a $C_1$–$C_{18}$-alkoxy or halogen or is aralkyl where the alkyl is of 1–12 carbons which is unsubstituted or substituted in the aryl moiety by $C_1$–$C_4$-alkyl, $C_1$–$C_4$-alkoxy or halogen,
- $R^2$ and $R^3$ are each hydrogen or a $C_1$–$C_4$-alkyl, and A is nitrogen or $CR^4$, where
- $R^4$ is hydrogen, a $C_1$–$C_4$- alkyl or halogen.

3. The compound of claim 1 wherein $R^1$ is n-$C_8H_{17}$, $R^2$ is $CH_3$, $R^3$ is $CH_3$, $R^4$ is H and A is $CR^4$.

4. The compound of claim 1 wherein $R^1$ is n-$C_8H_{17}$, $R^2$ is $CH_3$, $R^3$ is H and A is N.

5. The compound of claim 1 wherein $R^1$ is n-$C_9H_{19}$, $R^2$ is $CH_3$, $R^3$ is H and A is N.

6. The compound of claim 1 wherein $R^1$ is n-$C_9H_{19}$, $R^2$ is $CH_3$, $R^3$ is $CH_3$ and A is N.

7. The compound of claim 1 wherein $R^1$ is an unsubstituted alkyl of 7 to 10 carbon atoms.

* * * * *